(12) United States Patent
Shimada et al.

(10) Patent No.: US 10,413,170 B2
(45) Date of Patent: Sep. 17, 2019

(54) PERIMETER

(71) Applicant: KOWA COMPANY, LTD., Aichi (JP)

(72) Inventors: Satoshi Shimada, Tokyo (JP); Takuya Hara, Tokyo (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

(21) Appl. No.: 15/107,504

(22) PCT Filed: Dec. 22, 2014

(86) PCT No.: PCT/JP2014/083898
§ 371 (c)(1),
(2) Date: Jun. 23, 2016

(87) PCT Pub. No.: WO2015/098828
PCT Pub. Date: Jul. 2, 2015

(65) Prior Publication Data
US 2016/0317024 A1 Nov. 3, 2016

(30) Foreign Application Priority Data
Dec. 24, 2013 (JP) .................. 2013-265028

(51) Int. Cl.
*A61B 3/024* (2006.01)
*A61B 3/00* (2006.01)
(52) U.S. Cl.
CPC ............ *A61B 3/024* (2013.01); *A61B 3/0025* (2013.01); *A61B 3/0058* (2013.01)
(58) Field of Classification Search
CPC ........... A61B 3/024; A61B 3/02; A61B 3/022; A61B 3/0025; A61B 3/0058; A61B 3/102
(Continued)

(56) References Cited

U.S. PATENT DOCUMENTS

2009/0033870 A1\* 2/2009 Hangai .................. A61B 3/102
351/206

FOREIGN PATENT DOCUMENTS

JP 2009-34480 A 2/2009

OTHER PUBLICATIONS

International Search Report, corresponding to International Application No. PCT/JP2014/083898, dated Mar. 31, 2015.
(Continued)

*Primary Examiner* — Evan P Dzierzynski
*Assistant Examiner* — Alberto J Betancourt
(74) *Attorney, Agent, or Firm* — Duane Morris LLP

(57) ABSTRACT

Through the present invention, a perimetry result is obtained for a position on a retina surface designated as a position to be tested. As illustrated in the drawing, "the position of a ganglion cell (RGC)" and "the position of a photoreceptor cell (C) for sending information to the ganglion cell (RGC)" are offset on the retina surface (macular part). Here, when position (P1) is designated as a test position for testing the functioning of a ganglion cell at position (P1), the perimeter of the present invention finds "the position (P2) of the photoreceptor cell for sending information to the ganglion cell at position (P1)," presents a visual target at position (P2) rather than position (P1), and tests a visual field. The information of the visual target is sent to the ganglion cell at position (P1), and the functioning of the ganglion cell can therefore be tested. The test result is correlated with the position (P1) and displayed, and the ganglion cell at the designated position (P1) can be therefore be tested.

17 Claims, 4 Drawing Sheets

(58) Field of Classification Search
 USPC ....... 351/200, 205, 212, 221, 222, 224, 225, 351/226
 See application file for complete search history.

(56) References Cited

OTHER PUBLICATIONS

J. Sjostrand, et al., "Quantitative Estimations of Foveal and extra-Foveal Retinal Circuitry in Humans", Vision Research, 199, vol. 39, p. 2987-2998.
Shinji Okubo, "Gantei Taio Shiyakei", Journal of the Eye, 2010, vol. 27, No. 11, pp. 1545 and 1546.
J. Sjosatrand, et al., "Morphometric Study of Displacement of Retinal Ganglion Cells Subserving Cones within the Human Fovea", Spriger-Verlag 1999, vol. 237, p. 1014-1023.

\* cited by examiner

FIG. 2

(PRIOR ART)

| DISPLACEMENT OF PHOTORECEPTOR CELL (mm/deg) | TOTAL DISPLACEMENT (mm/deg) | DISPLACEMENT OF GANGLION CELL (mm/deg) | AREA RATIO ($A_C/A_{RGC}$) |
|---|---|---|---|
| 0.25/0.90 | 0.31/1.12 | 0.56/2.02 | 0.44 |
| 0.50/1.80 | 0.36/1.29 | 0.86/3.09 | 0.58 |
| 1.00/3.60 | 0.34/1.21 | 1.34/4.81 | 0.75 |
| 1.50/5.40 | 0.20/0.74 | 1.70/6.14 | 0.88 |
| 2.00/7.20 | 0.10/0.37 | 2.10/7.57 | 0.95 |

PERIMETER

TECHNICAL FIELD

The invention relates to a perimeter for measuring a visual field of an examinee through presentation of stimuli into his (her) visual field.

BACKGROUND ART

A retinal ganglion cell (RGC), which may be referred to as "the ganglion cell" hereinafter, is a type of neuron located near the inner surface of the retina of the eye, and receives visual information from photoreceptors (cone cells and rod cells) via two intermediate neuron types; bipolar cells and retina amacrine cells. If the ganglion cell is damaged, a person has glaucoma that leads to narrow visual field and vision loss. So, it is important to find weakly functioning ganglion cells at an early stage and stop the progress of the disease and deterioration of the ganglion cells. As one of methods of finding deterioration of the function of the ganglion cell is a perimetry, and perimeters having various kinds of structures for carrying out such a perimetry have been proposed (see the Patent-related document 1, for instance).

It has been found that there is a closer correlation between the deterioration of the function of the above-mentioned ganglion cell and thickness of retinal inner layer (GCC thickness, the thickness of Ganglion Cell Complex), and the thickness of the retinal inner layer is thin at a portion where the function of the ganglion cell is weak. Under these situations, a method for the perimetry is to find portions where retinal inner thickness is thin based on various kinds of fundus images, such as an OCT image and a GCC thickness map made from the OCT image, and to present a stimulus on the portion so as to carry out the perimetry preferentially thereon.

PRIOR ART

Patent-Related Document

[Patent-related document 1]: Japanese Patent No.5231085

Non-Patent-Related Document

[Non Patent-related document 1]: Johann Sjostrand. Quantitative estimations of foveal and extra foveal retinal circuitry in humans, Vision Research 39 (1999) 2987-2998

[Non Patent-related document 2]: Johann Sjostrand and other three. [Morphometric Study of the displacement of retinal ganglion cells subserving cones within the human fovea], Graefe's archive for clinical and experimental ophthalmology, Springer Berlin/Heidelberg, Vol.237, Number 12/December, 1999.

DISCLOSURE OF INVENTION

Problems to be Solved by Invention

It has been found that a positional offset exists between a position where the ganglion cell is located (the position on the retina surface) and a position where a photoreceptor cell for sending information to the ganglion cell (that is, the photoreceptor cell linked with the ganglion cell) is located (the position on the retina surface) (see NON PATENT-RELATED DOCUMENTS 1 and 2, for instance). FIG. 4 is a schematic diagram that typically shows such a positional relation between the photoreceptor cell and the ganglion cell (shows a coordinate system along a surface of the retina). In the figure, the origin is a center of the retina, and the vertical axis and the horizontal axis indicate an eccentricity from a retinal center (unit of the vertical axis is degee (deg) and unit of the horizontal axis is millimeter (mm)). As shown in the figure, each ganglion cell RGC is offset in a direction going away from the retinal center in relation to the linked photoreceptor cell C. It has been found that the amount of the offset is not constant, and is the greatest near the center of the retina and becomes smaller further away from the center of the retina, and there is almost no positional offset on the outer side of a macula.

A conventional problem is that even if the portion where the inner layer thickness of the retina (see, P1, for instance) is found in the macula of the retina and the stimulus is presented onto the portion P1 for the perimetry on the ganglion cell of the portion P1, the information regarding the stimulus received by the photoreceptor cell existing at the portion P1 is sent to the ganglion cell at the position P3 away from the center of the retina so as to test the ganglion cell at the position P3, thus it is not possible to test the ganglion cell of the designated portion P1.

An object of the invention is to provide the perimeter for solving the above-mentioned problem.

Means for Solving Problems

A first aspect of the invention is a perimeter (1) for measuring a visual field of an examinee through presentation of stimuli into his (her) visual field, comprising:

a position memory (3) that stores a position on a retinal surface where a ganglion cell (RGC of FIG. 4) is located and a position on the retinal surface where a photoreceptor cell (c) for sending information to the ganglion cell (RGC) is located, correlating with each other;

a test-position input (2) for inputting a position (P1 of FIG. 4) on the retinal surface to be tested ("the test position" hereinafter);

a position obtaining portion (4) that obtains the position (P2) of the photoreceptor cell (C) that sends information to the ganglion cell (RGC) at the test position (P1) inputted through the test-position input (2) based upon the test position (P1) and data stored in the position memory (3);

a stimulus presentator (5) that presents a stimulus to the position (P2) obtained through the position obtaining portion (4);

an operation portion (6) to be operated by an examinee who perceives the presented stimulus;

a visual field judger (7) that judges the visual field of the examinee based upon a response from the examinee through the operation portion (6); and a judged-result output (8) that displays the result judged through the visual field judger (7), correlating with the test position (P1).

A second aspect of the invention is a perimeter (1), wherein the test-position input (2) has a monitor (20), a fundus image output (21) that displays a fundus image on the monitor (20), and a position designator (22) that designates the test position (P1) on the fundus image.

A third aspect of the invention is a perimeter (1), further comprising a memory (23) that stores data showing a distribution of inner layer thickness of the retina of the examinee, wherein the data that shows the distribution of the inner layer thickness of the retina is displayed on the monitor (20).

The number in parentheses shows the corresponding element in the drawings for the sake of convenience, accordingly, the descriptions are not restricted and bound by the descriptions on the drawings.

EFFECTS OF INVENTION

According to the 1st and 2nd aspects of the invention, it is possible to grasp "the position designated to be tested" and "the function of the ganglion cell located on the position", correlating with each other.

According to the 3rd aspect of the invention, an abnormality area is easily identified and it is possible to properly initiate the perimetry on the abnormality area.

BRIEF DESCRIPTION OF DRAWINGS

FIG. 2 is a table that shows a positional relation between a photoreceptor cell and a ganglion cell.

PREFERRED EMBODIMENT

Figure 1:
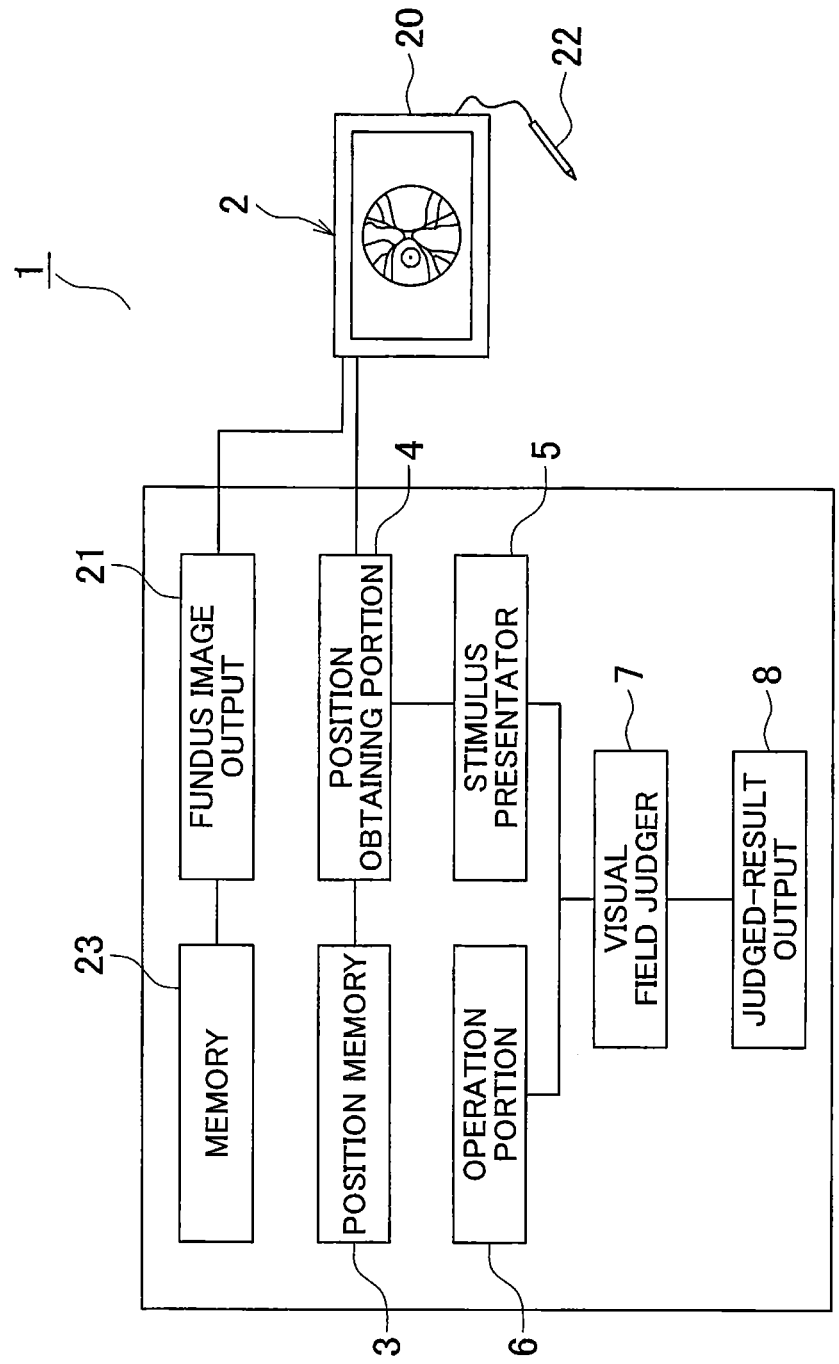
FIG. 1 is a block diagram that shows an example of a perimeter according to the present invention.

An embodiment of the present invention is now explained, referring to appended figures FIGS. 1 through 4.

In the specification, a position on a retinal surface to be tested, that is, the position to be tested that designated by an examiner and the position on which function of the ganglion cell is to be tested, is referred to as "a test position", and a position on the retinal surface onto which stimuli are actually presented at the time of the perimetry is referred to as "a stimulus presentation position".

A perimeter according to the invention exemplarily shown with a reference number 1, measures a visual field of an examinee through presentation of the stimulus onto a desired stimulus presentation position in his (her) visual field (the above-mentioned stimulus presentation position). The perimeter 1 has a test-position input 2 for inputting the above-mentioned test position. Preferably, this test-position input 2 is comprised of a monitor 20, a fundus image output 21 for displaying a fundus image, that is, the image of the fundus surface, on the monitor 20 (see S1 of FIG. 3) , and a position designator 22 for designating the test position on the fundus image, such as a mouse and a touch-pen (see S2 of FIG.3). Besides, the perimeter 1 is provided with a memory 23 for storing data of a distribution of an inner layer thickness of the retina of the examinee so as to display the data that shows the inner layer thickness of the retina on the monitor 20. Concretely speaking, the monitor 20 displays the fundus image that shows the distribution of the inner layer thickness of the retina, such as a GCC thickness map of OCT, or both usual fundus image that does not show the distribution of the inner layer thickness of the retina and data from which the distribution of the inner layer thickness of the retina is found, such as a sectional image of the fundus, so that it is possible to easily identify an abnormality area and properly designate the perimetry at the abnormality area.

In such a case, the above-mentioned fundus image may be imaged just before the perimetry, or may be one that has been imaged and stored in a filing unit (a memory). The monitor 20 may display the test position or the stimulus presentation position.

Figure 3:
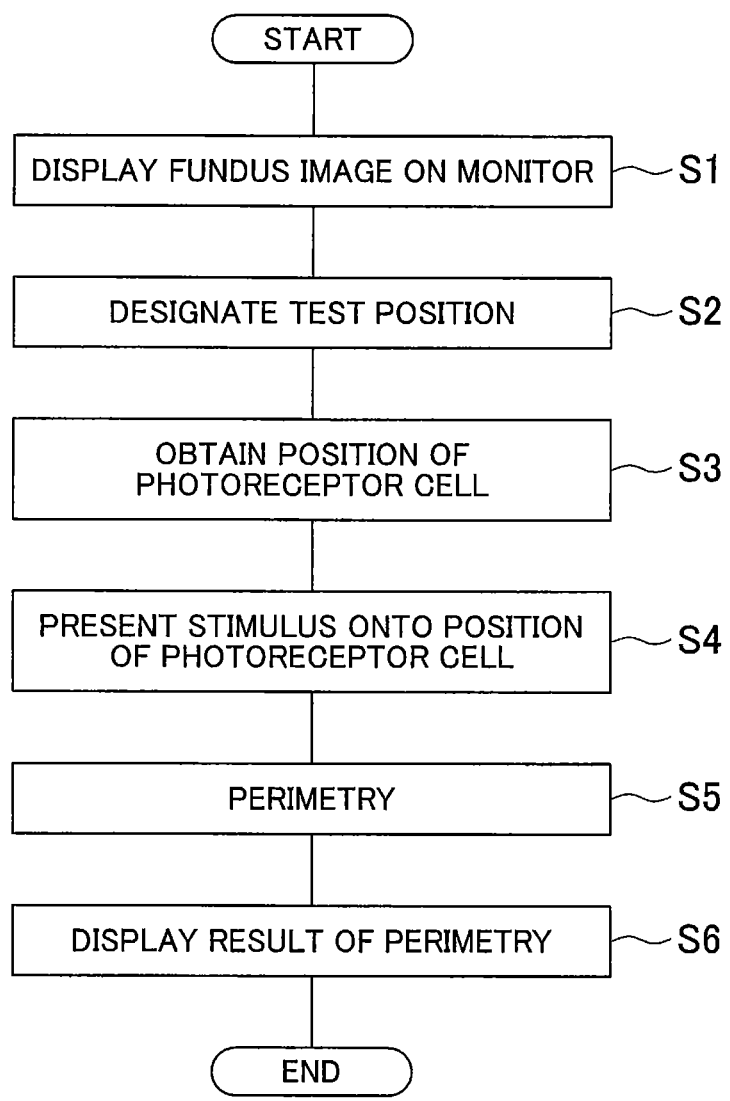
FIG. 3 is a flow chart that shows an example of a way of carrying out the perimetry with the perimeter according to the present invention.
Figure 4:
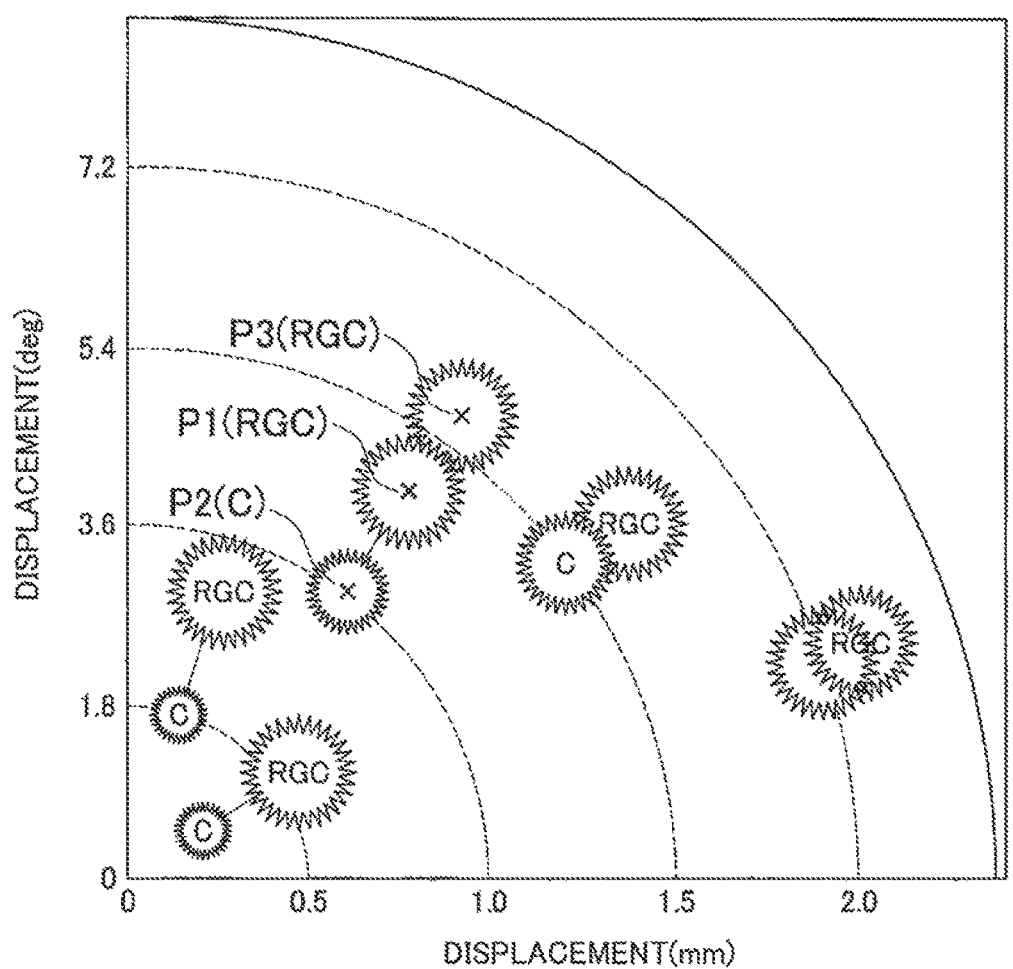
FIG. 4 is a schematic diagram that typically shows the positional relation between the photoreceptor cell and the ganglion cell.

And, the perimeter according to the invention has a position memory 3 for storing "the position on the retina surface where the ganglion cell (see RGC of FIG.4) is located" correlated with "the position on the retina surface where a photoreceptor cell (see "C" of FIG.4) that sends information to the ganglion cell RGC is located", and a position obtaining portion 4 (see S3 of FIG. 3) for obtaining a position P2 of the photoreceptor cell C that sends information to a ganglion cell RCG existing at the test position P1 inputted by the test-position input 2 (that is, the stimulus presentation position) based on the test position, such as P1 of FIG. 4, and the data stored in the position memory 3. The data stored in the position memory 3 are a table shown in NON PATENT-RELATED DOCUMENT 1 (see the table of FIG. 2), for instance. Such a table shows displacement of the photoreceptor cell from the retinal center, the total displacement, the displacement of the ganglion cell and area ratio of the photoreceptor cell and the ganglion cell. Preferably, the position memory 3 stores "the displacement of the photoreceptor cell" and "the displacement of the ganglion cell". In this table, one of values of the displacement of the photoreceptor cell is 0.25/0.90, and this value indicates the photoreceptor cell 0.25mm away from the center of the retina (that is, 0.90 deg away from the center of the retina). The displacement of the ganglion cell at the same line in the table is O. 56/2.02, and indicates the position where the ganglion cell linked to the photoreceptor cell is located is O. 56 mm away from the center of the retina (that is, 2.02 deg away from the center of the retina) . Then, "the distance from the center of the retina to the stimulus presentation position P2 (mm or deg)" is obtained based upon the distance (mm or deg) from "the center of the retina to the test position P2". Then, the stimulus presentation position P2 is specified on the assumption that the position P2 of the photoreceptor cell C is offset in a direction closer to the center of the retina rather than the position P1 of the ganglion cell RGC.

The above-mentioned NON PATENT-RELATED DOCUMENT 2 also describes the relation between the displacement of the photoreceptor cell regarding the center of the retina and the displacement of the ganglion cell.

This paper states the displacement A of the photoreceptor cell and the displacement B of the ganglion cell have the following relationship.

$$B=1.29*(A+0.046)^{0.67}$$

If the test position P1 inputted through the test-position input 2 (the displacement from the center of the retina) is substituted for B of the above-mentioned equation so as to obtain A, the position onto which the stimulus is to be presented is obtained. In this case, the data excluding the above-mentioned may be used as long as the data shows the positional relation between the photoreceptor cell and the ganglion cell.

Besides, the perimeter 1 according to the present invention has a stimulus presentator 5 for presenting the stimulus at the position obtained through the position obtaining portion 4 (the above-mentioned stimulus presentation position that is not the position P1 where the ganglion cell RGC is located, but the position P2 where the photoreceptor cell linked to the ganglion cell RGC is located), and an operation portion 6 to be operated by the examinee who perceives the presented stimulus, and a visual field judger 7 for judging the visual field of the examinee based upon a response from the examinee through the operation portion 6, and is configured to carry out the perimetry (see S5 of FIG. 3).

Furthermore, the perimeter 1 according to the present invention has a judged-result output 8 (see S6 of FIG. 3) for displaying the result judged by the visual field judger 7 so as to correlate with the above-mentioned test position. Preferably, when displaying both, correlating with each other, it is possible to obtain information regarding the test position P1, the result of the perimetry and information as to at which test position the test result is obtained. The judged-result output 8 may be a monitor (the monitor 20 or the other monitors), such as a liquid crystal display, a printer and an output portion for sending information to an external monitor or a printer as long as it displays the judged result of the visual field and the test position so as to be correlated with each other. Besides, when the judged-result output 8 is the monitor, the stimulus presentation position may be simultaneously displayed with the test position. In such a case, the test position and the stimulus presentation position may be differentiated from each other by changing these colors. For instance, one is shown with red, the other is shown in blue, and the overlapped is shown with green. Furthermore, the test position and the stimulus presentation position may be alternately shown without simultaneous display (representation is switched through the operation of a mouse or the like). Moreover, the result judged by the visual field judger may be displayed so as to link with the stimulus presentation position as well as the representation linking to the test position.

According to the present invention, the position onto which the stimulus is presented through the stimulus presentator 5 is not "the test position P1 designated by the test-position input 2", but "the position P2 where the photoreceptor cell (that is, the photoreceptor cell that sends information to the ganglion cell located at the test position Pl) is located". The information of the presented stimulus is received by the photoreceptor cell C at the position P2 and is sent to the ganglion cell RGC at the position Pl, thereby judging function of the ganglion cell RGC at the position Pl. Accordingly, it is possible to grasp "the position P1 designated to be tested" and "the function of the ganglion cell RGC located at the position P1", correlating with each other. When a portion where the inner layer thickness of the retina is thin is designated as the test position, it is possible to judge the function of the ganglion cell RGC located at such a portion (the portion where the inner layer thickness of the retina is thin), to grasp "the structure of the retina (the inner layer thickness of the retina)" and "the function of the ganglion cell RGC", correlating with each other, and to grasp the relation between the thickness of the inner layer of the retina and the visual field.

The test-position input may automatically designate the test position as well as manual designation. In the above-mentioned embodiment, the fundus image is displayed on the monitor 20 of the test-position input 2, and the test position is manually designated through the position designator 22 on the monitor 20. The perimeter according to the invention may be configured that coordinate information of the abnormality area is obtained directly from the other inspection equipment, such as an OCT so as to automatically input (designate) the test position.

EXPLANATION OF REFERENCE NUMBERS

1 . . . perimeter
2 . . . test-position input
3 . . . position memory
4 . . . position obtaining portion
5 . . . stimulus presentator
6 . . . operation portion
7 . . . visual field judger
8 . . . judged-result output
20 . . . monitor
21 . . . fundus image output
22 . . . position designator
23 . . . memory
C . . . photoreceptor cell
P1 . . . test position
P2 . . . position of photoreceptor cell
RGC . . . ganglion cell

The invention claimed is:

1. A perimeter for measuring a visual field of an examinee through presentation of stimuli into the examinee's visual field wherein the examinee has a retinal surface, the perimeter comprising:
a fundus image output portion for displaying an image of the examinee's fundus;
a test-position input device for inputting a test position on the image of the examinee's fundus displayed on the fundus image output portion, wherein the test position represents the location of the ganglion cell to be tested on the examinee's retinal surface;
a position obtaining portion that determines the location of a photoreceptor cell on the retinal surface that is linked to the ganglion cell to be tested based on the inputted test position and data stored in a position memory,
wherein the data stored in the position memory is a predetermined position relationship between ganglion cell locations and the locations of their linked photoreceptor cells correlated to one another;
a stimulus presentator that presents a stimulus to the retinal surface of the examinee at the location of the photoreceptor cell;
an operation portion to be operated by the examinee for providing a response when the examinee perceives the presented stimulus;
a visual field judger that judges the visual field of the examinee based upon the response provided by the examinee through the operation portion; and
a judged-result output that displays the result judged by the visual field judger and the corresponding test position.

2. The perimeter according to claim 1, further comprising a memory that stores data showing a distribution of inner layer thickness of the retina of the examinee, wherein the data that shows the distribution of the inner layer thickness of the retina is displayed on the fundus image output portion.

3. The perimeter according to claim 1, wherein the data stored in the position memory comprises displacement of the photoreceptor cell and displacement of the ganglion cell with respect to the center of the retinal surface.

4. A method for measuring a visual field of an examinee using a perimeter comprising the steps:
(a) displaying an image of the examinee's fundus on the fundus image output portion;
(b) receiving a test position information identified on the image of the examinee's fundus by an examiner, wherein the test position representing the location of a ganglion cell to be tested on the retinal surface of the examinee, wherein the ganglion cell has a photoreceptor cell linked thereto and positioned at a location on the retinal surface that is different from the ganglion cell;

(c) determining the location of the photoreceptor cell on the retinal surface that is linked to the ganglion cell, based on a predetermined positional relationship between ganglion cell locations and the locations of their linked photoreceptor cells;

(d) presenting a stimulus at the location of the photoreceptor cell on the retinal surface of the examinee for the examinee to respond whether or not the examinee perceives the stimulus; and (e) monitoring the examinee's response to the stimulus to judge the examinee's visual field.

5. The method of claim 4, wherein the predetermined positional relationship between ganglion cell locations and the locations of their linked photoreceptor cells is defined by the equation:

$$B = 1.29*(A+0.046)^{0.67}$$

where B is the test position and A is the location of the linked photoreceptor cell.

6. The method of claim 4, further comprising the step of:
judging the visual field of the examinee based on the examinee's response to the stimulus; and
outputting results of the judging step.

7. The method of claim 6, wherein the results of the judging step comprises simultaneously displaying the visual field of the examinee, the test position, and the location of the photoreceptor cell on a monitor.

8. The method of claim 6, further comprising a step of displaying a fundus image on a monitor before step (a), and wherein in step (a), the examiner inputs the test position information by designating the test position on the fundus image using a position designator.

9. The method of claim 8, wherein the fundus image shows a distribution of the inner layer thickness of the retina to enable the examiner to identify an abnormality area in the retina and initiate the perimetry at the abnormality area.

10. The method of claim 8, wherein the fundus image displayed on the monitor is one that does not show a distribution of the inner layer thickness of the retina and displaying a sectional image of the fundus on the monitor along with the fundus image to enable the examiner to identify an abnormality area in the retina and initiate the perimetry at the abnormality area.

11. A perimeter for measuring a visual field of an examinee through presentation of stimuli into the examinee's visual field wherein the examinee has a retinal surface, the perimeter comprising:
a fundus image output portion for displaying an image of the examinee's fundus;
a microprocessor; and
a non-transitory, machine readable storage medium encoded with computer program code for performing a method for measuring the visual field of the examinee, wherein when the microprocessor executes the computer program code, the perimeter performs a method comprising:

(a) displaying an image of the examinee's fundus on the fundus image output portion;

(b) receiving a test position information identified on the image of the examinee's fundus by an examiner, wherein the test position representing the location of a ganglion cell to be tested on the retinal surface of the examinee, wherein the ganglion cell has a photoreceptor cell linked thereto and positioned at a location on the retinal surface that is different from the ganglion cell;

(c) determining the location of the photoreceptor cell on the retinal surface that is linked to the ganglion cell, based on a predetermined positional relationship between ganglion cell locations and the locations of their linked photoreceptor cells;

(d) presenting a stimulus at the location of the photoreceptor cell on the retinal surface of the examinee for the examinee to respond whether or not the examinee perceives the stimulus; and (e) monitoring the examinee's response to the stimulus to judge the examinee's visual field.

12. The perimeter of claim 11, wherein the predetermined positional relationship between ganglion cell locations and the locations of their linked photoreceptor cells is defined by the equation:

$$B = 1.29*(A+0.046)^{0.67}$$

where B is the test position and A is the location of the linked photoreceptor cell.

13. The perimeter of claim 11, further comprising the step of:
judging the visual field of the examinee based on the examinee's response to the stimulus; and
outputting results of the judging step.

14. The perimeter of claim 13, wherein the results of the judging step comprises simultaneously displaying the visual field of the examinee, the test position, and the location of the photoreceptor cell on a monitor.

15. The perimeter of claim 13, further comprising a step of displaying a fundus image on a monitor before step (a), and wherein in step (a), the examiner inputs the test position information by designating the test position on the fundus image using a position designator.

16. The perimeter of claim 15, wherein the fundus image shows a distribution of the inner layer thickness of the retina to enable the examiner to identify an abnormality area in the retina and initiate the perimetry at the abnormality area.

17. The perimeter of claim 15, wherein the fundus image displayed on the monitor is one that does not show a distribution of the inner layer thickness of the retina and displaying a sectional image of the fundus on the monitor along with the fundus image to enable the examiner to identify an abnormality area in the retina and initiate the perimetry at the abnormality area.

\* \* \* \* \*